United States Patent [19]

Kreutzer et al.

[11] Patent Number: 5,512,695

[45] Date of Patent: Apr. 30, 1996

[54] BIDENTATE PHOSPHITE AND NICKEL CATALYST COMPOSITIONS FOR HYDROCYANATION OF MONOOLEFINS

[75] Inventors: Kristina A. Kreutzer, Wilmington, Del.; Wilson Tam, Boothwyn, Pa.

[73] Assignee: E. I. Du Pont de Nemours and Company, Wilmington, Del.

[21] Appl. No.: 400,163

[22] Filed: Mar. 7, 1995

Related U.S. Application Data

[63] Continuation-in-part of Ser. No. 227,802, Apr. 14, 1994, abandoned.

[51] Int. Cl.$^6$ .................................................. C07C 253/10
[52] U.S. Cl. .......................... 558/338; 502/121; 502/162; 502/213
[58] Field of Search ................................................ 558/338

[56] References Cited

U.S. PATENT DOCUMENTS

| | | | |
|---|---|---|---|
| 3,496,215 | 2/1970 | Drinkard, Jr. et al. | 260/465.8 |
| 3,496,217 | 2/1970 | Drinkard, Jr. et al. | 260/465.8 |
| 3,496,218 | 2/1970 | Drinkard, Jr. | 260/465.8 |
| 3,536,748 | 10/1970 | Drinkard, Jr. et al. | 260/465.9 |
| 3,631,191 | 12/1971 | Kane et al. | 260/439 |
| 3,655,723 | 4/1972 | Drinkard, Jr. | 260/465.3 |
| 3,676,481 | 7/1972 | Chia | 260/465.9 |
| 3,766,237 | 10/1973 | Chia et al. | 260/465.3 |
| 3,773,809 | 11/1973 | Walter | 260/465.8 |
| 3,775,461 | 11/1973 | Drinkard, Jr. et al. | 260/465.3 |
| 3,846,461 | 11/1974 | Shook, Jr. | 260/439 R |
| 3,847,959 | 11/1974 | Shook, Jr. | 260/439 R |
| 3,903,120 | 9/1975 | Shook, Jr. et al. | 260/439 R |
| 4,371,474 | 2/1983 | Rapoport | 558/338 |
| 4,599,206 | 7/1986 | Billig et al. | 558/85 |
| 4,688,651 | 8/1987 | Dysart | 175/371 |
| 4,717,775 | 1/1988 | Billig et al. | 568/454 |
| 4,769,498 | 9/1988 | Billig et al. | 568/454 |
| 4,774,353 | 9/1988 | Hall et al. | 558/335 |
| 4,874,884 | 10/1989 | McKinney et al. | 558/338 |
| 5,202,297 | 4/1993 | Lorz et al. | 502/106 |
| 5,312,957 | 5/1994 | Casalnuovo et al. | 558/410 |
| 5,449,807 | 9/1995 | Druliner | 558/338 |

FOREIGN PATENT DOCUMENTS

WO93/03839   3/1993   WIPO.

OTHER PUBLICATIONS

Tolman, C. A. et al, *Advances in Catalysis,* 33, 1–45, 1985.
Baker, M. J. et al, *J. Chem. Soc. Chem. Comm.,* 1292–1293, 1991.
Baker, M. J. et al, *J. Chem. Soc. Chem. Commun.,* 803–804, 1991.
Cuny, et al., *J. Am. Chem. Soc.,* 115, 2066–2068, 1993.

*Primary Examiner*—Joseph Paul Brust

[57] ABSTRACT

Processes for hydrocyanation of nonconjugated aliphatic monoolefins or monoolefins conjugated to an ester group utilizing a catalyst precursor composition comprising an unsymmetrical bidentate phosphite ligand and zero-valent nickel, preferably in the presence of a Lewis acid promoter, to produce a terminal organonitrile. Catalyst precursor compositions are also disclosed.

13 Claims, No Drawings

5,512,695

BIDENTATE PHOSPHITE AND NICKEL CATALYST COMPOSITIONS FOR HYDROCYANATION OF MONOOLEFINS

This application is a continuation-in-part of Ser. No. 08/227,802, filed Apr. 14, 1994 and now abandoned.

FIELD OF THE INVENTION

The invention generally relates to processes and catalyst precursor compositions useful for the hydrocyanation of monoolefins. In particular, the invention relates to the hydrocyanation of monoolefins using catalyst precursor compositions comprising zero-valent nickel and unsymmetrical bidentate phosphite ligands.

BACKGROUND OF THE INVENTION

Hydrocyanation catalyst systems, particularly pertaining to the hydrocyanation of olefins, are known in the art. For example, systems useful for the hydrocyanation of butadiene to form pentenenitrile (PN) and in the subsequent hydrocyanation of pentenenitrile (PN) to form adiponitrile (AND), are known in the commercially important nylon synthesis field.

The hydrocyanation of olefins using transition metal complexes with monodentate phosphite ligand is documented in the prior art. See for example; U.S. Pat. Nos. 3,496,215, 3,631,191, 3,655,723 and 3,766,237, and Tolman, C. A.; McKinney, R. J.; Seidel, W. C.; Druliner, J. D.; and Stevens, W. R.; Advances in Catalysis, 33, 1, 1985.

The hydrocyanation of activated olefins such as with conjugated olefins (e.g., butadiene and styrene) and strained olefins (e.g., norbornene) proceeds without the use of a Lewis acid promoter, while hydrocyanation of unactivated olefins such as 1-octene and 3-pentenenitrile requires the use of a Lewis acid promoter. Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters.

U.S. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. U.S. Pat. No. 4,874,884 discloses a process for producing ADN by the zero-valent nickel catalyzed hydrocyanation of pentenenitriles in the presence of a synergistic combination of promoters selected in accordance with the reaction kinetics of the ADN synthesis.

Bidentate phosphite ligands similar to those used in the present invention for the hydrocyanation of monoolefins have been shown to be useful ligands in the hydrocyanation of activated olefins. See, for example: Baker, M. J., and Pringle, P. G.; J. Chem. Soc., Chem. Commun., 1292, 1991; Baker, M. J.; Harrison, K. N.; Orpen, A. G.; Pringle, P. G.; and Shaw, G.; J. Chem. Soc.; Chem. Commun., 803, 1991, Union Carbide, WO 93,03839. Also, similar ligands have been disclosed with rhodium in the hydroformylation of functionalized olefins; Cuny et al., J. Am. Chem. Soc. 1993, 115, 2066.

The present invention provides novel processes and catalyst precursor compositions which are rapid, selective, efficient and stable in the hydrocyanation of monoolefins. Other objects and advantages of the present invention will become apparent to those skilled in the art upon reference to the detailed description which hereinafter follows.

SUMMARY OF THE INVENTION

The present invention provides a process for hydrocyanation, comprising reacting a nonconjugated acyclic aliphatic monoolefin or a monoolefin conjugated to an ester group; e.g., methyl pent-2-eneoate, with a source of HCN in the presence of a catalyst precursor composition comprising zero-valent nickel and a bidentate phosphite ligand of Formula I,

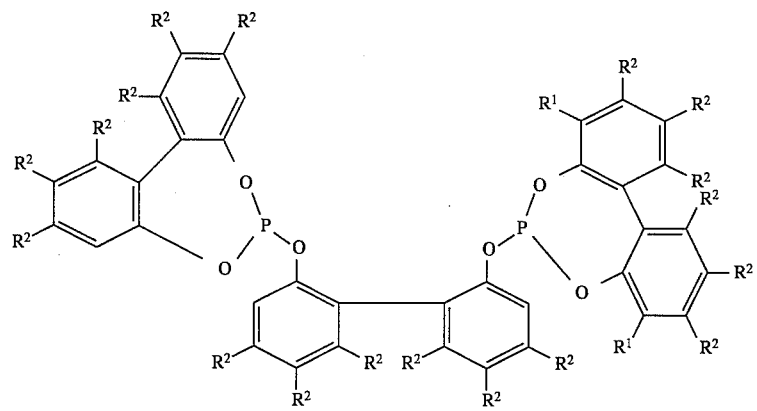

Formula I wherein
each $R^1$ is independently a secondary or tertiary substituted hydrocarbyl of 3 to 12 carbon atoms;
each $R^2$ is independently, H, X wherein X is Cl, F or Br, a $C_1$ to $C_{12}$ alkyl, or $OR^3$ wherein $R^3$ is $C_1$ to $C_{12}$ alkyl;
to produce a terminal organonitrile. Preferably, the reaction is carried out in the presence of a Lewis acid promoter.

The present invention also provides a process for hydrocyanation comprising reacting a nonconjugated acyclic aliphatic monoolefin or a monoolefin conjugated to an ester group; e.g., methyl pent-2-eneoate, with a source of HCN in the presence of a catalyst precursor composition comprising zero-valent nickel and a bidentate phosphite ligand selected from the group consisting of Formulas II–VI as set forth below:

Formula II

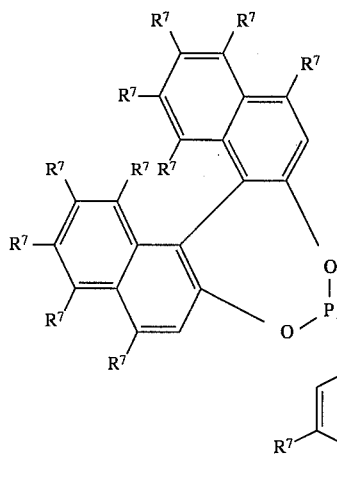 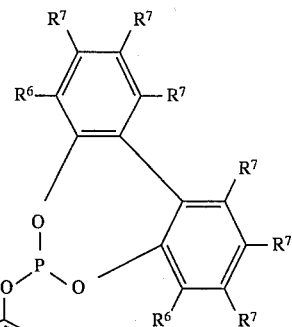

wherein
  each $R^6$ is independently a secondary or tertiary substituted hydrocarbyl of 3 to 12 carbon atoms; and
  each $R^7$ is independently H, X wherein X is Cl, F or Br, a $C_1$ to $C_{12}$ alkyl, or $OR^8$ wherein $R^8$ is $C_1$ to $C_{12}$ alkyl;

each $R^{10}$ is independently H, X wherein X is Cl, F or Br, a $C_1$ to $C_{12}$ alkyl, or $OR^8$ wherein $R^8$ is $C_1$ to $C_{12}$ alkyl; and
  each $R^{11}$ is independently a branched or straight chain alkyl of up to 12 carbon atoms;

Formula III

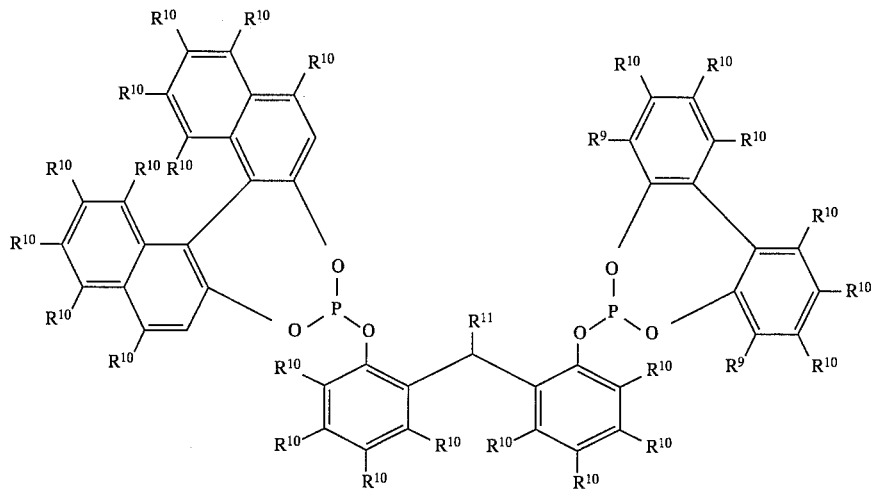

wherein
  each $R^9$ is independently a secondary or tertiary substituted hydrocarbyl of 3 to 12 carbon atoms;

Formula IV

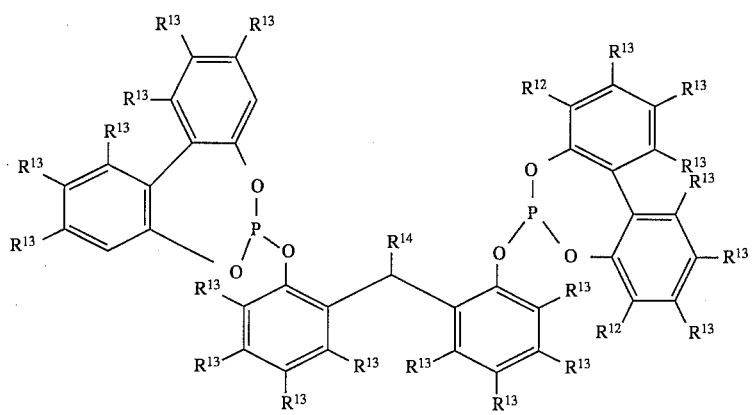

wherein
  each $R^{12}$ is independently a secondary or tertiary substituted hydrocarbyl of 3 to 12 carbon atoms;
  each $R^{13}$ is independently H, X wherein X is Cl, F or Br, a $C_1$ to $C_{12}$ alkyl, or $OR^8$ wherein $R^8$ is $C_1$ to $C_{12}$ alkyl; and
  each $R^{14}$ is independently a branched or straight chain alkyl of up to 12 carbon atoms;

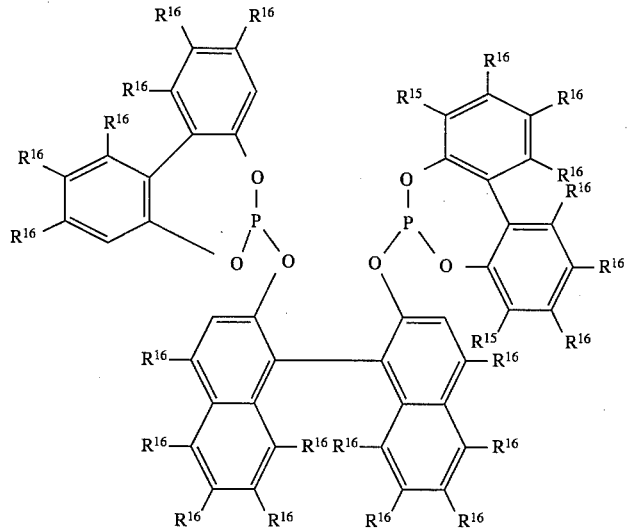

Formula V wherein
  each $R^{15}$ is independently a secondary or tertiary substituted hydrocarbyl of 3 to 12 carbon atoms; and
  each $R^{16}$ is independently H, X wherein X is Cl, F or Br, a $C_1$ to $C_{12}$ alkyl, or $OR^8$ wherein $R^8$ is $C_1$ to $C_{12}$ alkyl; and

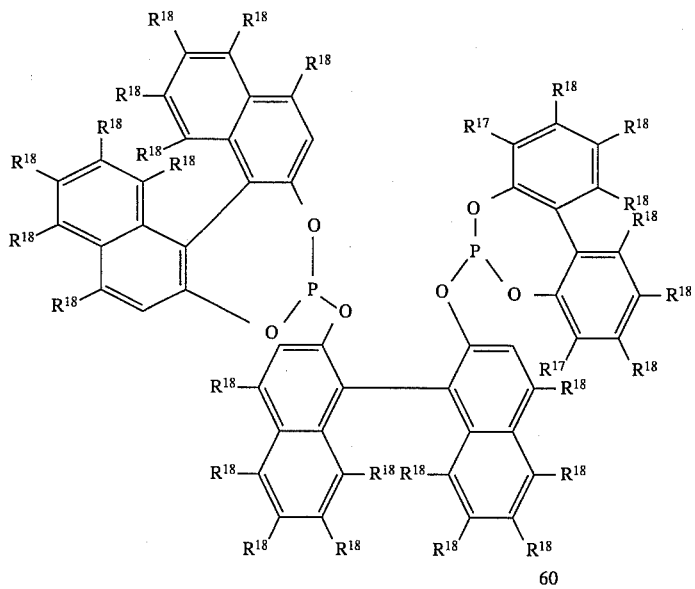

wherein
  each $R^{17}$ is independently a secondary or tertiary substituted hydrocarbyl of 3 to 12 carbon atoms; and
  each $R^{18}$ is independently H, X wherein X is Cl, F or Br, a $C_1$ to $C_{12}$ alkyl, or $OR^8$ wherein $R^8$ is $C_1$ to $C_{12}$ alkyl;

to produce a terminal organonitrile. Preferably, the reaction is carried out in the presence of a Lewis acid promoter.

The monoolefins of the above-identified processes are described by Formulas VII or IX, and the corresponding terminal organonitrile compounds produced are described by Formulas VIII or X, respectively.

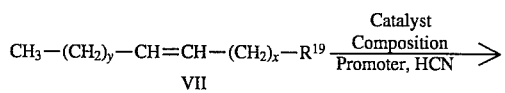

VII

Formula VI

-continued

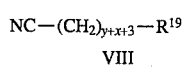

VIII wherein
  $R^{19}$ is H, CN, $CO_2R^{20}$, or perfluoroalkyl;

y is 0 to 12;
x is 0 to 12 when $R^{19}$ is H, $CO_2R^{20}$ or perfluoroalkyl;
x is 1 to 12 when $R^{19}$ is CN; and
$R^{20}$ is alkyl; or

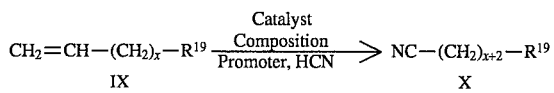

wherein
$R^{19}$ is H, CN, $CO_2R^{20}$, or perfluoroalkyl;
x is 0 to 12 when $R^{19}$ is H, $CO_2R^{20}$ or perfluoroalkyl;
x is 1 to 12 when $R^{19}$ is CN; and
$R^{20}$ is alkyl.

The present invention further provides a catalyst precursor composition comprising zero-valent nickel and an unsymmetrical bidentate phosphite ligand of Formula I,

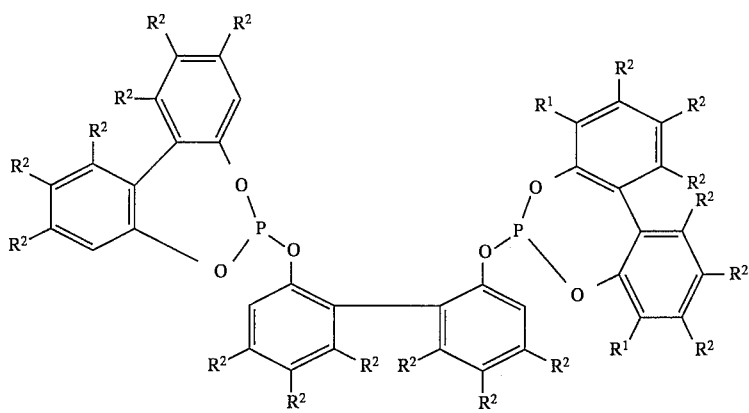

Formula I wherein
each $R^1$ is independently a secondary or tertiary substituted hydrocarbon of 3 to 12 carbon atoms; and
each $R^2$ is independently H, X wherein X is Cl, F or Br, a $C_1$ to $C_{12}$ alkyl, or $OR^3$ wherein $R^3$ is $C_1$ to $C_{12}$ alkyl.

The present invention further provides a catalyst precursor composition comprising zero-valent nickel and an unsymmetrical bidentate phosphite ligand selected from the group consisting of Formulas II–VI as set forth below:

each $R^6$ is independently a secondary or tertiary substituted hydrocarbyl of 3 to 12 carbon atoms; and
each $R^7$ is independently H, X wherein X is Cl, F or Br, a $C_1$ to $C_{12}$ alkyl, or $OR^8$ wherein $R^8$ is $C_1$ to $C_{12}$ alkyl;

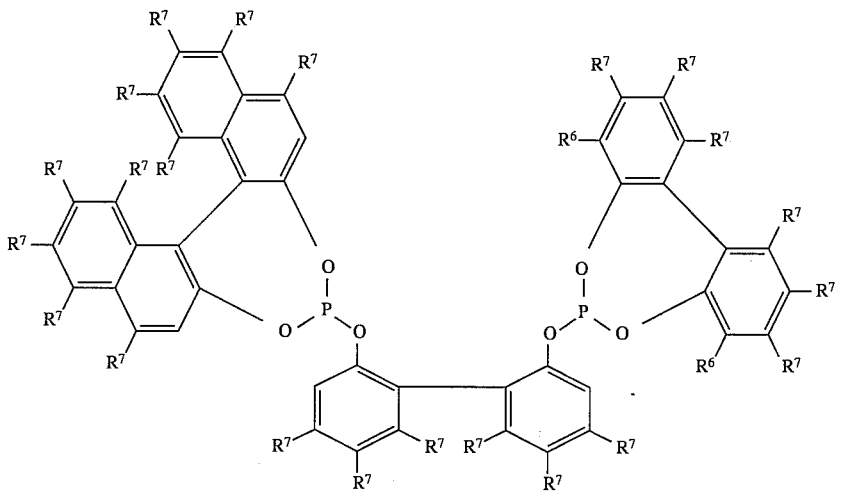

Formula II wherein

Formula III

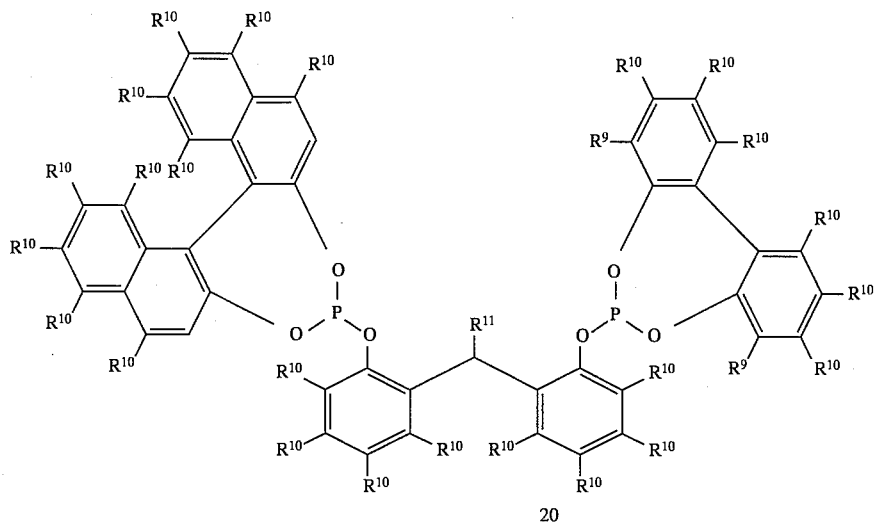

wherein
- each $R^9$ is independently a secondary or tertiary substituted hydrocarbyl of 3 to 12 carbon atoms;
- each $R^{10}$ is independently H, X wherein X is Cl, F or Br, a $C_1$ to $C_{12}$ alkyl, or $OR^8$ wherein $R^8$ is $C_1$ to $C_{12}$ alkyl; and
- each $R^{11}$ is independently a branched or straight chain alkyl of up to 12 carbon atoms;

- each $R^{12}$ is independently a secondary or tertiary substituted hydrocarbyl of 3 to 12 carbon atoms;
- each $R^{13}$ is independently H, X wherein X is Cl, F or Br, a $C_1$ to $C_{12}$ alkyl, or $OR^8$ wherein $R^8$ is $C_1$ to $C_{12}$ alkyl; and
- each $R^{14}$ is independently a branched or straight chain alkyl of up to 12 carbon atoms;

Formula IV

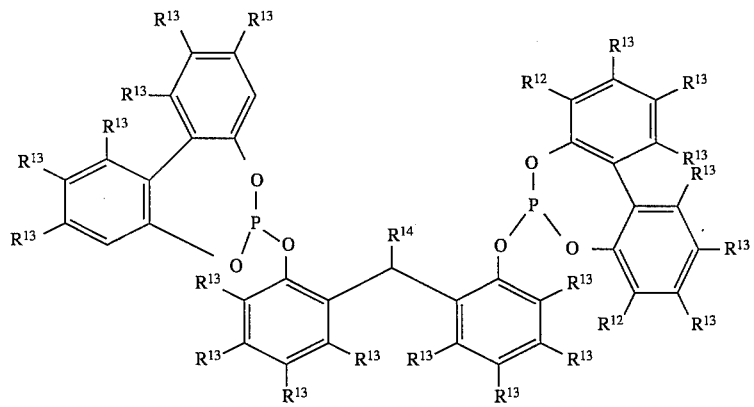

wherein

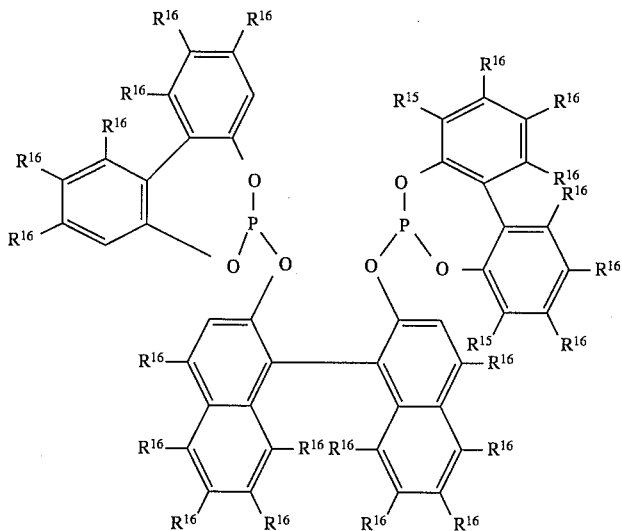

Formula V wherein
each $R^{15}$ is independently a secondary or tertiary substituted hydrocarbyl of 3 to 12 carbon atoms; and
each $R^{16}$ is independently H, X wherein X is Cl, F or Br, a $C_1$ to $C_{12}$ alkyl, or $OR^8$ wherein $R^8$ is $C_1$ to $C_{12}$ alkyl; and

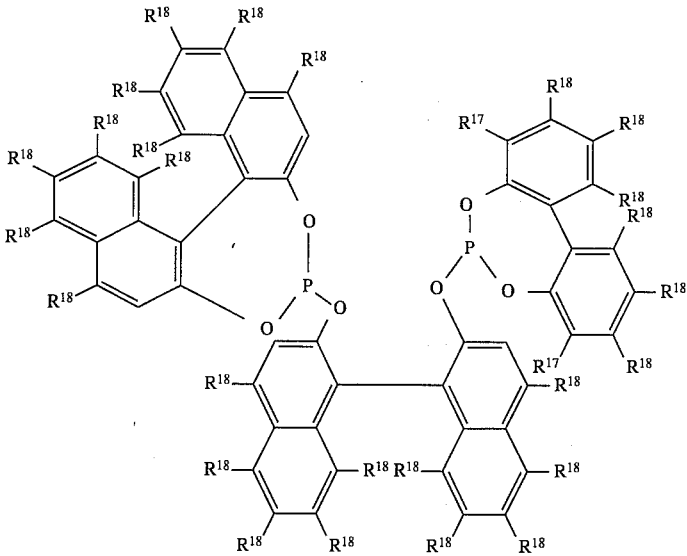

wherein
each $R^{17}$ is independently a secondary or tertiary substituted hydrocarbyl of 3 to 12 carbon atoms; and
each $R^{18}$ is independently H, X wherein X is Cl, F or Br, a $C_1$ to $C_{12}$ alkyl, or $OR^8$ wherein $R^8$ is $C_1$ to $C_{12}$ alkyl.

Preferably, the catalyst precursor compositions of Formulas I–VI further comprise a Lewis acid promoter.

DETAILED DESCRIPTION OF THE PREFERRED EMBODIMENTS

The catalyst precursor compositions of the invention are comprised of a bidentate phosphite ligand and zero-valent nickel. The preferred ligand of the invention is described below by Formula I, wherein each $R^2$ is independently H, or Formula VI a $C_1$ to $C_{12}$ alkyl, or $OR^3$ wherein $R^3$ is a $C_1$ to $C_{12}$ alkyl. Alkyl includes straight chain or branched groups. $R^3$ can be primary, secondary or tertiary; examples include methyl, ethyl, isopropyl and t-butyl. Each $R^2$ may be the same or different. In the preferred ligand, all $R^2$ groups are H, except for the two $R^2$ groups meta to the $R^1$ groups. These $R^2$ groups are $OR^3$ wherein $R^3$ is methyl. $R^1$ is a secondary or tertiary substituted hydrocarbyl group containing up to single bond carbon atoms. In the preferred ligand, both $R^1$ groups are tertiary butyl.

Formula I

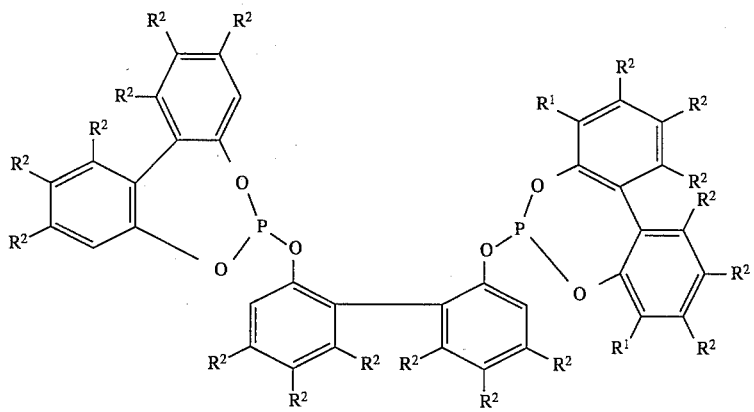

As used herein, the terms "secondary or tertiary substituted" refer to the first carbon of the hydrocarbyl which is attached to the ring. The term "hydrocarbyl" generally refers to a straight chain, branched or aryl carbon structure containing single, double or triple bonds, and substituted accordingly with hydrogen.

Applicants have referred to the catalyst composition of the invention as a "precursor" composition only to indicate that, in all likelihood, during the hydrocyanation reaction the structure of the active catalyst composition may in fact be complexed to an olefin.

The preferred ligands of the invention (i.e., Formula I) may be prepared by a variety of methods known in the art, for example see descriptions in WO 93,03839, U.S. Pat. No. 4,769,498; U.S. Pat. No. 4,688,651, J. Amer. Chem. Soc., 115, 2066, 1993. The reaction of 2,2'-biphenol with phosphorus trichloride gives 1,1'-biphenyl-2,2'-diyl phosphorochloridite. The reaction of this chloroidite with 2,2'-dihydroxy-3,3'-di-t-butyl-5,5'-dialkoxy-1,1'-biphenyl in the presence of triethylamine gives the preferred bidentate phosphite ligand wherein $R^1$ is t-butyl.

Other bidentate phosphite ligands of the invention are described above by Formulas II–VI. While these ligands may not be as presently preferred as Formula I, they nevertheless are considered useful ligands of the present invention. These ligands may be prepared by a variety of methods known in the art; for example, see U.S. Pat. No. 5,202,297, the contents of which are incorporated herein. According to U.S. Pat. No. 5,202,297, phosphorus trichloride is reacted with a diol to form a monochlorophosphite which is reacted with a diol to form a hydroxyl-substituted diorganophosphite. This diorganophosphite intermediate is reacted with another monochlorophosphite to give the unsymmetrical bidentate phosphite ligands of Formulas II–VI.

The zero-valent nickel can be prepared or generated according to techniques well known in the art (U.S. Pat. Nos. 3,496,217; 3,631,191; 3,846,461; 3,847,959; and 3,903,120 which are incorporated by reference). Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni(P(O-o-C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The nonconjugated acyclic aliphatic monoolefin substrates of the invention include unsaturated organic compounds containing from 2 to approximately 30 carbon atoms having at least one nonconjugated aliphatic carbon-carbon double bond. The 3-pentenenitrile and 4-pentenenitrile are especially preferred. As a practical matter, when the nonconjugated acyclic aliphatic monoolefins are used in accordance with this invention, up to about 10% by weight of the monoolefin may be present in the form of a conjugated isomer, which itself may be subject to hydrocyanation. For example, when 3-pentenenitrile is used, as much as 10% by weight thereof may be 2-pentenenitrile. Suitable unsaturated compounds include olefins and olefins substituted with groups which do not attack the catalyst, such as cyano. These unsaturated compounds include monoolefins containing from 2 to 30 carbons such as ethylene, propylene, butene-1, pentene-2, hexene-2, etc., nonconjugated diolefins such as allene, and substituted compounds such as 3-pentenenitrile, 4-pentenenitrile and methyl pent-3-enoate. The monoolefins may also be conjugated to an ester group such as methyl pent-2-enoate.

Two formulas are presented below which together describe these substrates of the invention; Formulas VII and IX. Substrates of Formula VII yield terminal organonitriles of Formula VIII, while Formula IX substrates will yield terminal organonitriles of Formula X.

$$CH_3—(CH_2)_y—CH=CH—(CH_2)_x—R^{19} \qquad \text{VII}$$

wherein $R^{19}$ is H, CN, $CO_2R^{20}$, or perfluoroalkyl;

y is 0 to 12;

x is 0 to 12 when $R^{19}$ is H, $CO_2R^{20}$ or perfluoroalkyl;

x is 1 to 12 when $R^{19}$ is CN; and $R^{20}$ is alkyl;

produces the terminal organonitrile product compound of Formula VIII $$NC—(CH_2)_{y+x+3}—R^{19} \qquad \text{VIII}$$

wherein $R^{19}$, y and x are as defined above.

$$CH_2=CH—(CH_2)_xR^{19} \qquad \text{IX}$$

wherein $R^{19}$ is H, CN, $CO_2R^{20}$, or perfluoroalkyl;

x is 0 to 12 when $R^{19}$ is H, $CO_2R^{20}$ or perfluoroalkyl;

x is 1 to 12 when $R^{19}$ is CN; and $R^{20}$ is alkyl, produces the terminal organonitrile product compound of Formula X $$NC-(CH_2)_{x+2}-R^{19} \qquad\qquad X$$

wherein $R^{19}$ and x are as defined above.

Perfluoroalkyl is defined as $C_zF_{2z+1}$ where z is 1 to 12.

Preferred substrates are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitrile, alkyl 2- and 3- and 4-penteneoates, and $C_zF_{2z+1}CH=CH_2$ (where z is 1 to 12).

The preferred products are terminal alkanenitriles, linear alkanedinitriles, linear alkane(nitrile)esters, and 3- (perfluoroalkyl) propionitrile. Most preferred products are adiponitrile, alkyl 5-cyanovalerate, and $C_zF_{2z+1}CH_2CH_2CN$ (where z is 1 to 12).

The present hydrocyanation process may be carried out by charging a reactor with all of the reactants, or preferably the reactor is charged with the catalyst precursor or catalyst components, the unsaturated organic compound, the promoter and the solvent to be used and the hydrogen cyanide added slowly. HCN may be delivered as a liquid or as a vapor to the reaction. Another technique is to charge the reactor with the catalyst, promoter, and the solvent to be used, and feed both the unsaturated compound and the HCN slowly to the reaction mixture. The molar ratio of unsaturated compound to catalyst generally is varied from about 10:1 to 2000:1.

Preferably, the reaction medium is agitated, such as by stirring or shaking. The cyanated product can be recovered by conventional techniques such as by distillation. The reaction may be run either batchwise or in a continuous manner.

The hydrocyanation reaction can be carried out with or without a solvent. The solvent should be liquid at the reaction temperature and pressure and inert towards the unsaturated compound and the catalyst. Generally, such solvents are hydrocarbons such as benzene or xylene, or nitriles such as acetonitrile or benzonitrile. In some cases, the unsaturated compound to be hydrocyanated may serve as the solvent.

The exact temperature which is preferred is dependent to a certain extent on the particular catalyst being used, the particular unsaturated compound being used and the desired rate. Generally, temperatures of from −25° to 200° C. can be used, with from 0° to 150° C. being preferred.

Atmospheric pressure is satisfactory for carrying out the present invention and hence pressure of from about 0.05 to 10 atmospheres are preferred due to the obvious economic considerations although pressures of from 0.05 to 100 atmospheres can be used if desired.

HCN may be added to the reaction as vapor or liquid, or in a system utilizing a cyanohydrin as carrier. See, for example, U.S. Pat. No. 3,655,723 which is incorporated herein by reference.

Typically, the processes of this invention are carried out in the presence of one or more Lewis acid promoters which affect both the activity and selectivity of the catalyst system. However, it should be understood that the presence of a Lewis acid promoter is not deemed critical to the invention, although it is preferred. The promoter may be an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $COCl_2$, $CoI_2$, $FeCl_2$, $FeI_2$, $FeCl_3$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(i-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $BPh_3$, $TaCl_5$. Suitable promoters are further described in U.S. Pat. No. 3,496,217; U.S. Pat. No. 3,496,218; U.S. Pat. No. 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group).

U.S. Pat. No. 4,874,884 describes how synergistic combinations of promoters may be chosen to increase the catalytic activity of the catalyst system. Preferred promoters are $CdCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The amount of promoter to nickel present in the reaction may be in the range of 1:16 to 50:1.

EXAMPLES

The following non-limiting examples further embody and enable the processes and catalyst compositions of the invention. Generally, HCN reactions were done using the following procedure unless otherwise noted.

The mixtures were heated in a thermostatically controlled oil bath. HCN was delivered to the flask as an $HCN/N_2$ gas mixture by bubbling dry nitrogen gas through liquid HCN at 0° C. (maintained in an ice bath); this provides a vapor stream which is about 35% HCN (vol/vol). The rate of nitrogen gas flow determines the rate of HCN delivery. Sample analysis was carried out by gas chromatographic (GC) analysis.

Example 1

Synthesis of the Ligand of Formula I where each $R^2$ is $OCH_3$ and each $R^1$ is t-butyl (Ligand "A")

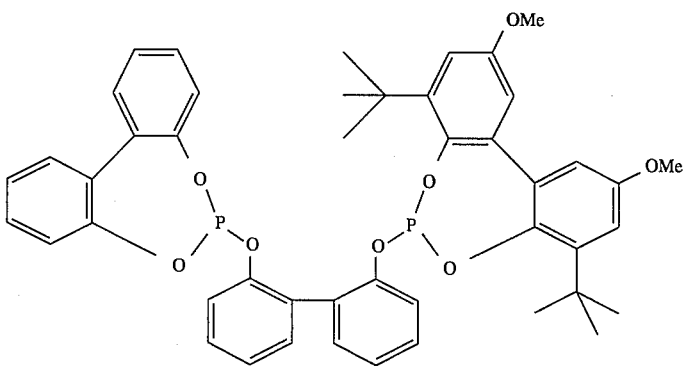

Ligand "A"

A solution of 2,2'-biphenol (28.1 g, 0.151 mol) in 49 mL phosphorus trichloride was heated at reflux for 2 hours. The excess $PCl_3$ was removed by distillation. The residue was purified by vacuum distillation (140°–143° C. at 0.5 mm Hg) to give 30.70 g (81% yield) 1,1'-biphenyl-2,2'-diyl phosphorochloridite (as a clear viscous oil which solidified to a white solid upon standing at room temperature in an inert atmosphere for an extended period of time). $^{31}P\{^1H\}$NMR (121.4 MHz, $d_8$-toluene): δ 180.1 (s), 85% $H_3PO_4$ external reference. To a solution containing 1.018 g (2.84 mmoles) of 2,2'-dihydroxy-3,3'-di-t-butyl-5,5'-dimethoxy-1,1'-biphenyl and 0.575 g (5.68 mmoles) of $NEt_3$ in 15 ml of tetrahydrofuran (THF) was added 1.412 g (5.68 mmoles) of 1,1'-biphenyl-2,2'-diyl phosphorochloridite in 5 ml of THF. The mixture was stirred overnight at room temperature. The mixture was filtered through celite, washed with THF and solvent removed to give 2.2 g of white solid. $^{31}P\{^1H\}$ nmr (121.4 MHz, $C_6D_6$): 145.15 s and 138.5 s. $^1H$ nmr (300 MHz, $C_6D_6$): singlet at 3.15 and 1.3 along with aromatic resonances.

Example 2

Hydrocyanation of 3-Pentenenitrile with Ligand ("A"/Ni(COD)$_2$ wherein COD=bis (1,5-cyclooctadiene) ) nickel: $ZnCl_2$ promoter 340 mg of Ligand A and 40 mg of Ni(COD)$_2$ were dissolved in 5 ml of THF. The solvent was removed by rotary evaporation and 5 ml of 3PN and 10 mg of $ZnCl_2$ were added. The mixture was treated with HCN at a nitrogen flow rate of 12 cc/min and heated at 50°, 60°, 70°, 80° C. for 15 minutes at each temperature. After heating at 80° C., GC analysis indicated 24.3% adiponitrile (ADN), 5.6% 2-methyl-glutaronitrile (MGN), and 0.7% of 2-ethylsuccinonitrile (ESN).

Example 3

Synthesis of the Ligand of Formula I where each $R^2$ and each $R^1$ is t-pentyl (Ligand "B")

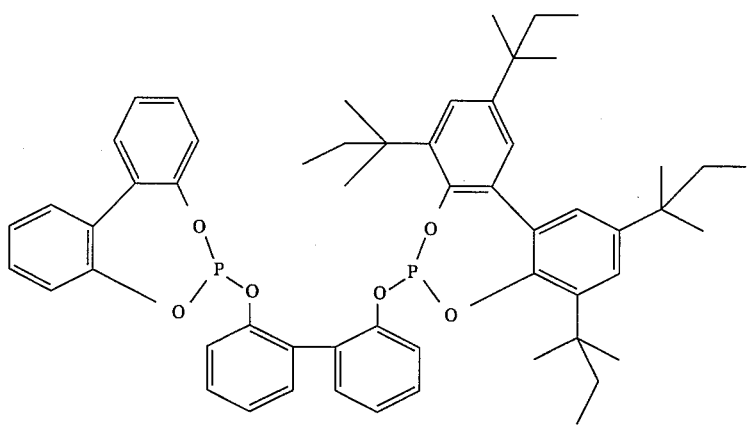

Ligand "B"

To a solution containing 2.0 g (8.0 mmoles) of 1,1'-biphenyl-2,2'-diyl phosphorochloridite in 10 ml of toluene was added dropwise a solution containing 1.86 g (3.99 mmoles) of 2,2'-dihydroxy-3,3',5,5'-tetra-t-pentyl-1,1'-biphenyl and 0.9 g (8.9 mmoles) of $NEt_3$ in 15 ml of toluene. The mixture was stirred overnight at room temperature and then refluxed under nitrogen for one hour. The mixture was filtered through celite, washed with toluene and solvent removed to give 3.8 g of white solid. $^{31}P\{^1H\}$ nmr (121.4 MHz, $C_6D_6$): 145.06 s and 137.1 s. $^1H$ nmr (300 MHz, $C_6D_6$): 2.0 (m, 4H), 1.8 (m, 4H), 1.5 (s, 12H), 1.3(s, 12H), 0.8 (m, 12H) along with aromatic resonances. The $^1H$ nmr spectrum also indicated some toluene.

Example 4

Hydrocyanations of 3-Pentenenitrile with Ligand "B"/Ni (COD)$_2$: $ZnCl_2$ promoter Carried out in a manner similar to Example 2, except 380 mg of Ligand B and 40 mg of Ni(COD)$_2$ were dissolved in 5 ml of THF. The solvent was removed by rotary evaporation and 5 ml of 3PN and 20 mg of $ZnCl_2$ were added. The mixture was treated with HCN at a nitrogen flow rate of 12 cc/min and heated at 50°, 60°, 70°, 80°, and 100° C. for 15 minutes at each temperature. After heating at 100° C., GC analysis indicated 7 2% ADN, 1.1% MGN, and 0.16% of ESN.

Example 5

Synthesis of the Ligand of Formula I where each $R^2$ and each $R^1$ are t-butyl (Ligand "C")

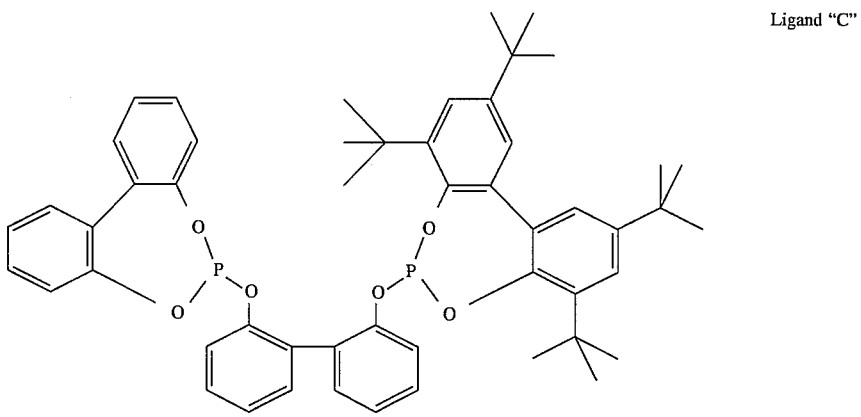
Ligand "C"

To a solution containing 1.2 g (4.8 mmoles) of 1,1'-biphenyl-2,2'-diyl phosphorochloridite in 20 ml of toluene was added dropwise a solution containing 1.0 g (2.4 mmoles) of 2,2'-dihydroxy-3,3',5,5'-tetra-t-butyl-1,1'-biphenyl and 1.2 g (11.8 mmoles) of $NEt_3$ in 20 ml of toluene. The mixture was refluxed under nitrogen for about two hours. The mixture was filtered through celite, washed with toluene and solvent removed to give 2.1 g of white solid. $^{31}P\ \{^1H\}$ nmr (121.4 MHz, $C_6D_6$): 145.2 d (J=4 Hz) and 137.77 d (J=4 Hz). $^1H$ nmr(300 MHz,$C_6D_6$): 1.77 s, 1.58 s along with aromatic resonances. The $^1H$ nmr spectrum also indicated some toluene.

Example 6

Hydrocyanations of 3-Pentenenitrile with Ligand "C"/Ni (COD)$_2$: ZnCl$_2$ promoter Carried out in a manner similar to Example 2, except 365 mg of Ligand C and 40 mg of Ni(COD)$_2$ were dissolved in 5 ml of THF. The solvent was removed by rotary evaporation and 5 ml of 3 PN and 20 mg of ZnCl$_2$ were added. The mixture was treated with HCN at a nitrogen flow rate of 12 cc/min and heated at 50°, 60°, 70°, 80°, and 100° C. for 15 minutes at each temperature. After heating at 100° C., GC analysis indicated 36.4% ADN, 7.0% MGN, and 1.0% of ESN.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than the foregoing specification, as indicating the scope of the invention.

We claim:

1. A process for hydrocyanation comprising reacting a monoolefin of Formula VII or IX with a source of HCN in the presence of a catalyst precursor composition comprising zero-valent nickel and a bidentate phosphite ligand of Formula I, to yield a terminal organonitrile of Formula VIII or X;

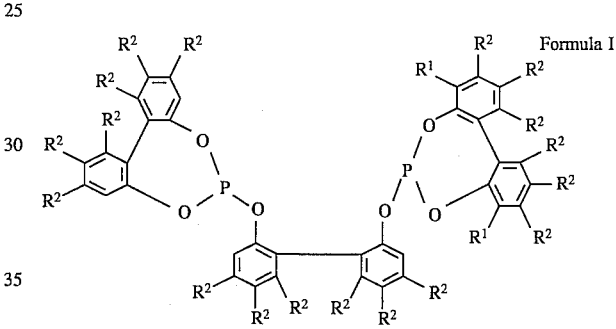

wherein
  each $R^1$ is independently a secondary or tertiary substituted hydrocarbyl of 3 to 12 carbon atoms; and
  each $R^2$ is independently, H, X wherein X is Cl, F or Br, a $C_1$ to $C_{12}$ alkyl, or $OR^3$ wherein $R^3$ is $C_1$ to $C_{12}$ alkyl;
  and wherein said monoolefin and terminal organonitrile are

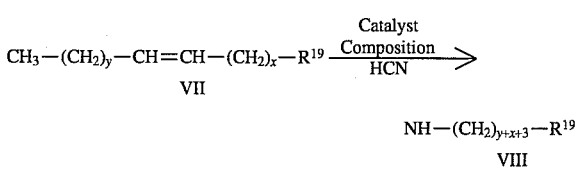

wherein
  $R^{19}$ is H, CN, $CO_2R^{20}$, or perfluoroalkyl;
  y is 0 to 12;
  x is 0 to 12 when $R^{19}$ is H, $CO_2R^{20}$ or perfluoroalkyl;
  x is 1 to 12 when $R^{19}$ is CN; and
  $R^{20}$ is alkyl; or

wherein
  $R^{19}$ is H, CN, $CO_2R^{20}$, or perfluoroalkyl;
  x is 0 to 12 when $R^{19}$ is H, $CO_2R^{20}$ or perfluoroalkyl;

x is 1 to 12 when $R^{19}$ is CN; and $R^{20}$ is alkyl.

2. The process of claim 1 wherein the reaction is carried out in the presence of a Lewis acid promoter.

3. The process of claims 1 or 2 wherein each $R^1$ is a tertiary substituted hydrocarbyl.

4. The process of claims 1 or 2 wherein each $R^1$ is a tertiary butyl group.

5. The process of claims 1 or 2 wherein all $R^2$ groups are H, except the $R^2$ groups meta to an $R^1$ group, said $R^2$ groups meta to an $R^1$ group are $OR^3$, and wherein $R^3$ is methyl.

6. The process of claims 1 or 2 wherein said monoolefin is selected from the group consisting of 3-pentenenitrile, 4-pentenenitrile, alkyl 2-pentenoate, alkyl 3-penteneoate, alkyl 4-pentenoate and $C_zF_{2z+1}CH=CH_2$ wherein z is 1 to 12.

7. The process of claim 2 wherein said Lewis acid promoter is selected from the group consisting of $ZnCl_2$, $CdCl_2$, $B(C_6H_5)_3$, and $(C_6H_5)SnX$ wherein x is $CF_3SO_3$, $CH_3C_6H_5SO_3$ or $(C_6H_5)_3BCN$.

8. The process of claims 1 or 2 wherein the ligand of Formula I is selected from the group consisting of Ligand A, Ligand B and Ligand C;

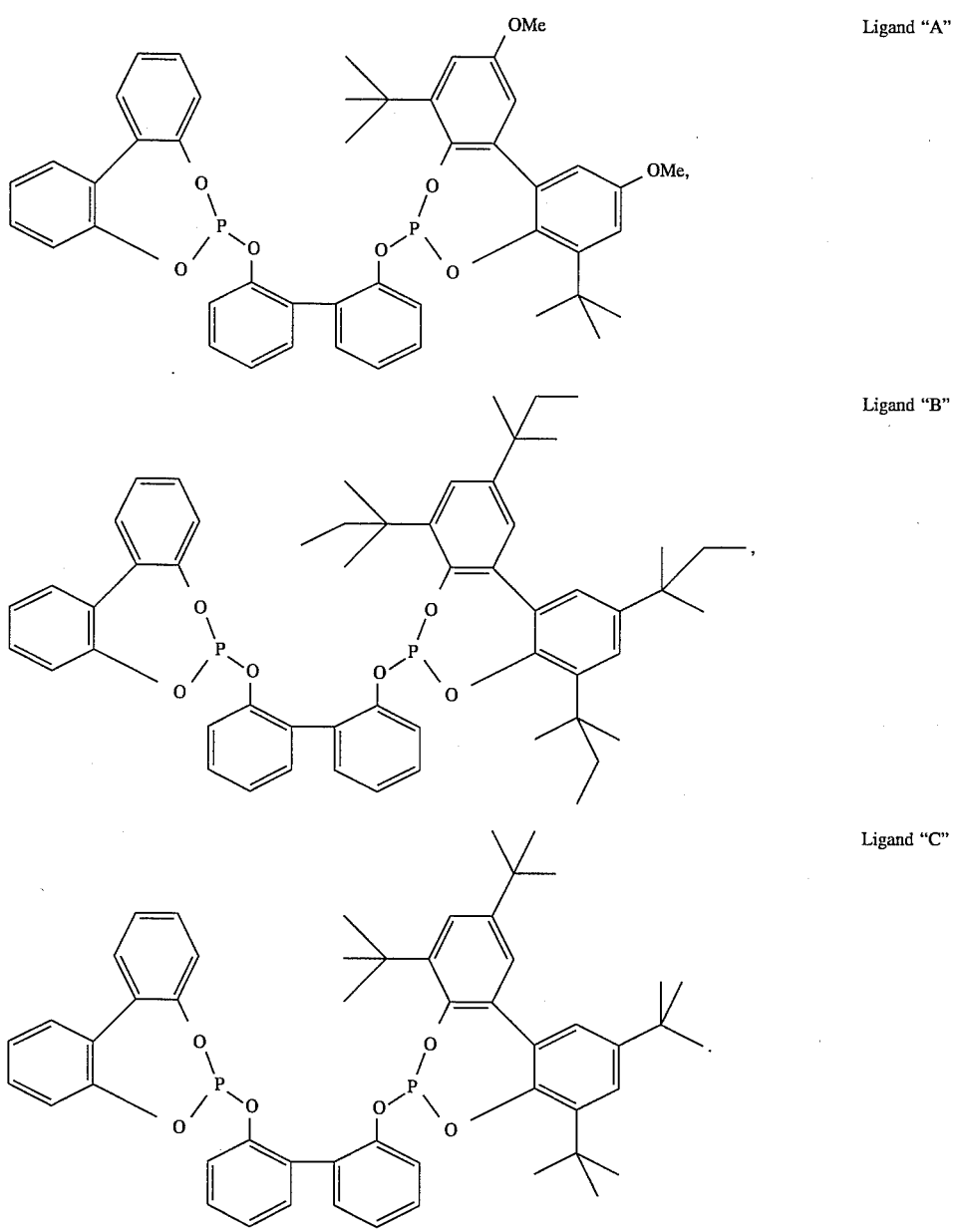

Ligand "A"

Ligand "B"

Ligand "C"

9. The process of claims 1 or 2 wherein each $R^1$ is t-butyl; all $R^2$ groups are H, except the $R^2$ groups meta to an $R^1$ group, said $R^2$ groups meta to an $R^1$ group are $OR^3$ and wherein $R^3$ is methyl; and the monoolefin is 3-pentenenitrile.

10. A process for hydrocyanation comprising reacting a nonconjugated acyclic aliphatic monoolefin or a monoolefin conjugated to an ester group; with a source of HCN in the presence of a catalyst precursor composition comprising zero-valent nickel and a bidentate phosphite ligand selected from the group consisting of Formulas II–VI as set forth below:

Formula II

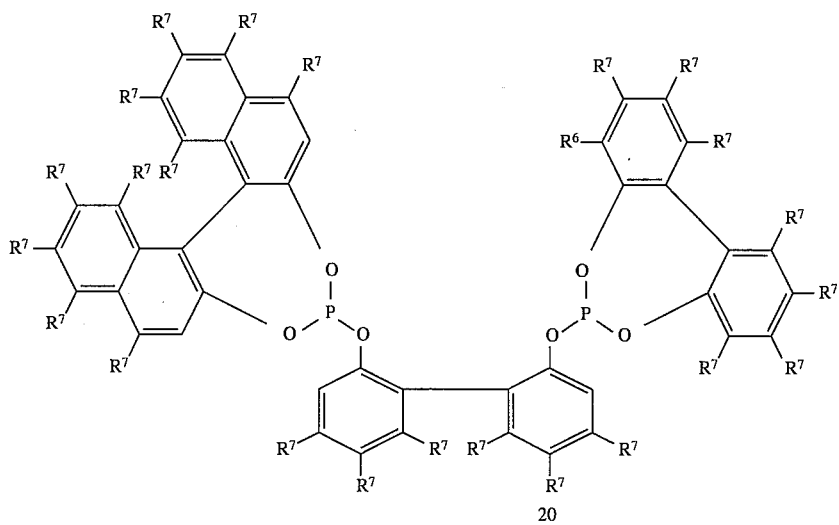

wherein
 each $R^6$ is independently a secondary or tertiary substituted hydrocarbyl of 3 to 12 carbon atoms; and
 each $R^7$ is independently H, X wherein X is Cl, F or Br, a $C_1$ to $C_{12}$ alkyl, or $OR^8$ wherein $R^8$ is $C_1$ to $C_{12}$ alkyl;

each $R^{10}$ is independently H, X wherein X is Cl, F or Br, a $C_1$ to $C_{12}$ alkyl, or $OR^8$ wherein $R^8$ is $C_1$ to $C_{12}$ alkyl; and each $R^{11}$ is independently a branched or straight chain alkyl of up to 12 carbon atoms;

Formula III

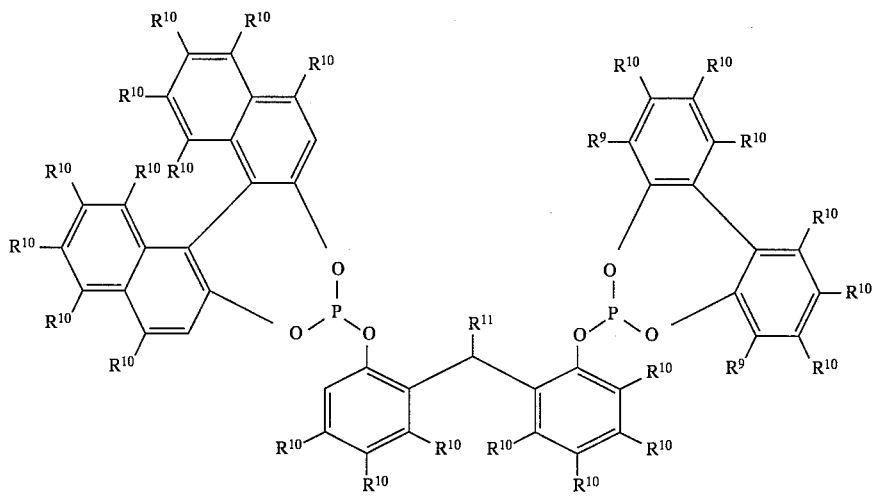

wherein
 each $R^9$ is independently a secondary or tertiary substituted hydrocarbyl of 3 to 12 carbon atoms;

Formula IV

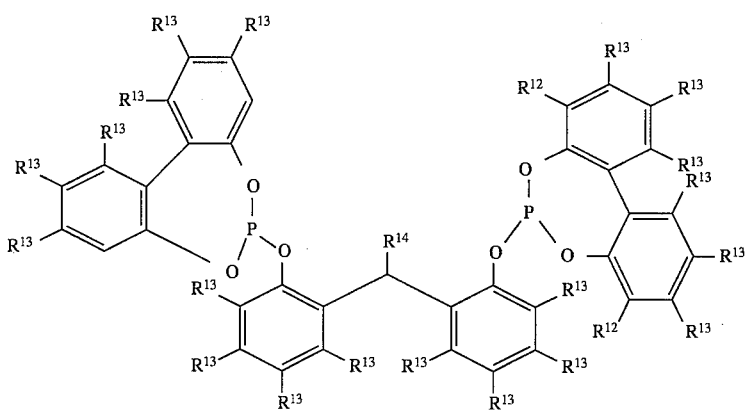

wherein
- each $R^{12}$ is independently a secondary or tertiary substituted hydrocarbyl of 3 to 12 carbon atoms;
- each $R^{13}$ is independently H, X wherein X is Cl, F or Br, a $C_1$ to $C_{12}$ alkyl, or $OR^8$ wherein $R^8$ is $C_1$ to $C_{12}$ alkyl; and
- each $R^{14}$ is independently a branched or straight chain alkyl of up to 12 carbon atoms;

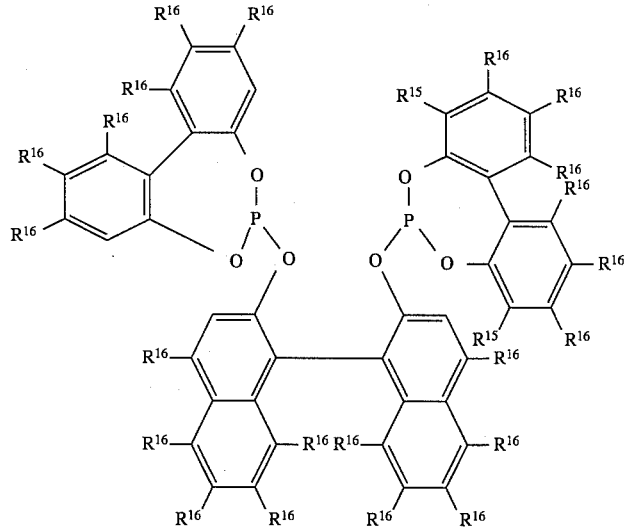

Formula V wherein
- each $R^{15}$ is independently a secondary or tertiary substituted hydrocarbyl of 3 to 12 carbon atoms; and
- each $R^{16}$ is independently H, X wherein X is Cl, F or Br, a $C_1$ to $C_{12}$ alkyl, or $OR^8$ wherein $R^8$ is $C_1$ to $C_{12}$ alkyl; and

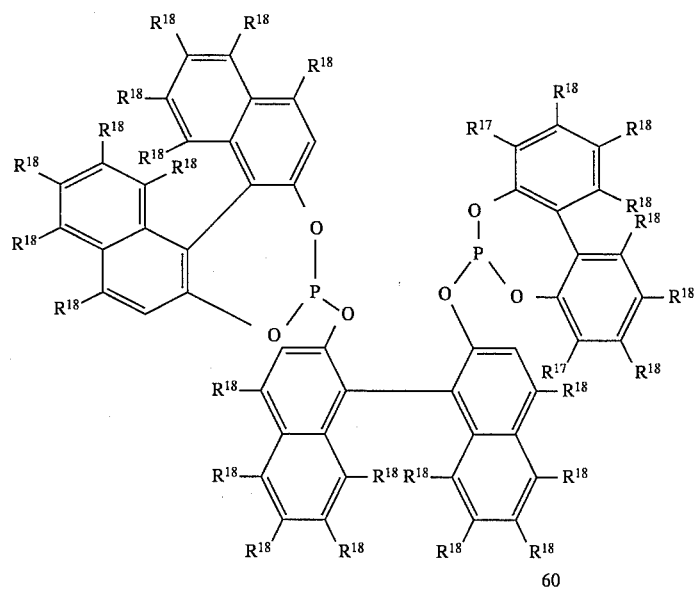

Formula VI wherein
- each $R^{17}$ is independently a secondary or tertiary substituted hydrocarbyl of 3 to 12 carbon atoms; and
- each $R^{18}$ is independently H, X wherein X is Cl, F or Br, a $C_1$ to $C_{12}$ alkyl, or $OR^8$ wherein $R^8$ is $C_1$ to $C_{12}$ alkyl;

and wherein said reaction is carried out to produce a terminal organonitrile.

11. The process of claim 10 wherein the reaction is carried out in the presence of a Lewis acid promoter.

12. The process of claims 10 or 11 wherein said monoolefin is selected from the group consisting of 3-pentenenitrile, 4-pentenenitrile, alkyl 2-pentenoate, alkyl 3-pentenoate, alkyl 4-pentenoate and $C_zF_{2z+1}CH\!=\!CH_2$ wherein z is 1 to 12.

13. The process of claim 11 wherein said Lewis acid promoter is selected from the group consisting of $ZnCl_2$, $CdCl_2$, $B(C_6H_5)_3$, and $(C_6H_5)SnX$ wherein x is $CF_3SO_3$, $CH_3C_6H_5SO_3$ or $(C_6H_5)_3BCN$.

* * * * *